US009464988B2

(12) United States Patent
Sando et al.

(10) Patent No.: US 9,464,988 B2
(45) Date of Patent: Oct. 11, 2016

(54) SURFACE PLASMON RESONANCE FLUORESCENCE MEASUREMENT DEVICE AND SURFACE PLASMON RESONANCE FLUORESCENCE MEASUREMENT METHOD

(75) Inventors: Yasuhiro Sando, Amagasaki (JP); Takahiro Mohri, Izumi (JP); Gou Yanagihara, Sakai (JP); Kenichi Miyata, Hachioji (JP); Masataka Matsuo, Hachioji (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/701,695

(22) PCT Filed: Jun. 2, 2011

(86) PCT No.: PCT/JP2011/003132
§ 371 (c)(1),
(2), (4) Date: Dec. 3, 2012

(87) PCT Pub. No.: WO2011/152064
PCT Pub. Date: Dec. 8, 2011

(65) Prior Publication Data
US 2013/0078146 A1    Mar. 28, 2013

(30) Foreign Application Priority Data

Jun. 4, 2010   (JP) .................................. 2010-128815

(51) Int. Cl.
*G01N 21/55*   (2014.01)
*G01N 21/64*   (2006.01)
(Continued)

(52) U.S. Cl.
CPC .............. *G01N 21/64* (2013.01); *G01N 21/55* (2013.01); *G01N 21/553* (2013.01); *G01N 21/648* (2013.01); *G01N 33/54373* (2013.01); *B82Y 20/00* (2013.01); *B82Y 35/00* (2013.01)

(58) Field of Classification Search
None
See application file for complete search history.

(56) References Cited

U.S. PATENT DOCUMENTS

| 5,437,840 A | 8/1995 | King et al. |
| 5,514,596 A | 5/1996 | King et al. |

(Continued)

FOREIGN PATENT DOCUMENTS

| JP | 7-311146 A | 11/1995 |
| JP | 2003-516536 A | 5/2003 |

(Continued)

OTHER PUBLICATIONS

International Search Report for International Application No. PCT/JP2011/003132, mailed Jun. 28, 2011, with English translation.

(Continued)

*Primary Examiner* — Neil N Turk
(74) *Attorney, Agent, or Firm* — Cantor Colburn LLP (57) ABSTRACT

A surface plasmon resonance fluorescence analysis device emits a light beam to a prism in which a metal film is formed on a prescribed surface while changing an angle of incidence relative to the metal film in a state in which the light beam is totally reflected, measures light generated on a surface of the metal film, determines an angle at which the light beam enters the metal film based on a change in intensity of the measured light, adjusts the emitting direction of the light beam so that the light beam enters the metal film at the determined angle of incidence, and measures fluorescence generated on the surface of the metal film in a state in which the light beam is emitted the adjusted direction.

8 Claims, 7 Drawing Sheets

(51) Int. Cl.
*G01N 21/552* (2014.01)
*G01N 33/543* (2006.01)
*G01N 21/65* (2006.01)
*B82Y 20/00* (2011.01)
*B82Y 35/00* (2011.01)

(56) References Cited

U.S. PATENT DOCUMENTS

| | | |
|---|---|---|
| 5,633,724 A | 5/1997 | King et al. |
| 6,753,188 B2 | 6/2004 | Perkins et al. |
| 2002/0182743 A1 | 12/2002 | Perkins et al. |
| 2006/0127278 A1* | 6/2006 | Gast et al. ............. 422/82.05 |

| | | | |
|---|---|---|---|
| 2009/0230308 A1 | | 9/2009 | Kimura |

FOREIGN PATENT DOCUMENTS

| | | |
|---|---|---|
| JP | 2006-208069 A | 8/2006 |
| JP | 2008-268063 A | 11/2008 |
| JP | 4370383 B2 | 11/2009 |

OTHER PUBLICATIONS

Extended European Search Report corresponding to Application No. 11789477.4-1554/2579023 PCT/JP2011/003132; Date of Mailing: May 13, 2016.

* cited by examiner

SURFACE PLASMON RESONANCE FLUORESCENCE MEASUREMENT DEVICE AND SURFACE PLASMON RESONANCE FLUORESCENCE MEASUREMENT METHOD

CROSS REFERENCE TO RELATED APPLICATIONS

This is a U.S. national stage of application No. PCT/JP2011/003132, filed on 2 Jun. 2011. Priority under 35 U.S.C. §119(a) and 35 U.S.C. §365(b) is claimed from Japanese Application No. 2010-128815, filed 4 Jun. 2010, the disclosure of which are also incorporated herein by reference.

TECHNICAL FIELD

The present invention relates to a surface plasmon resonance fluorescence analysis device and a surface plasmon resonance fluorescence analysis method that measure a specimen by causing a fluorescent substance contained in the specimen to emit light by utilizing the electric field of evanescent waves generated by surface plasmon resonance and then detecting the fluorescent light.

BACKGROUND ART

A known example of a conventional surface plasmon resonance fluorescence analysis device (also to be simply referred to as a "fluorescence analysis device") is described in Patent Document 1. In this analysis device, by generating surface plasmon resonance in a metal film deposited on a prism, an electric field (intensified electric field) that is intensified is formed in the vicinity of the surface of the metal film, and a specimen is detected with both high sensitivity and high accuracy by utilizing this intensified electric field.

Figure 6:
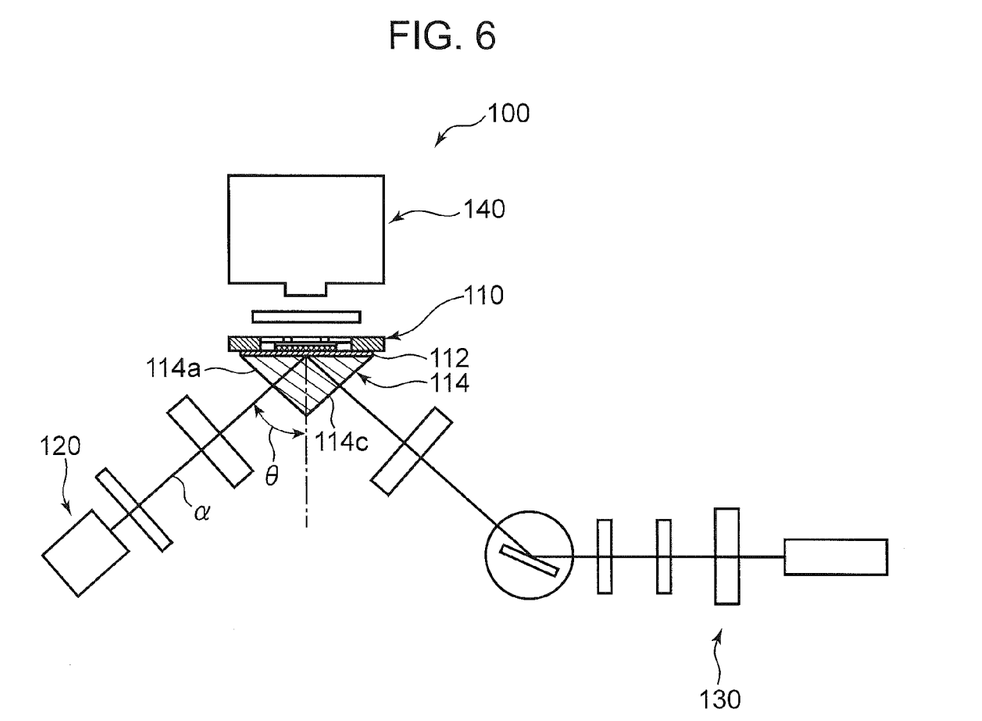
FIG. 6 is a schematic block diagram showing a surface plasmon resonance fluorescence analysis device of the prior art.
Figure 7:
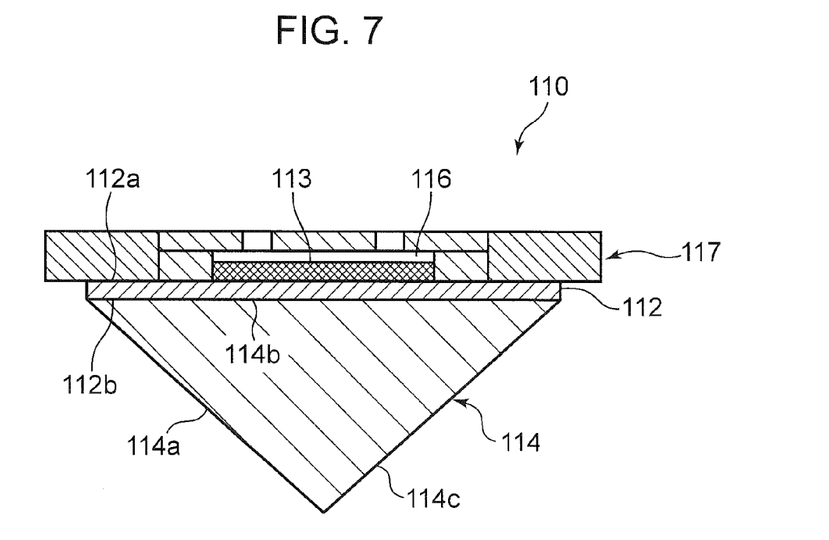
FIG. 7 is an enlarged longitudinal cross-sectional view showing the structure of a prism unit of the surface plasmon resonance fluorescence analysis device.

More specifically, as indicated in FIGS. 6 and 7, this fluorescence analysis device is provided with a prism unit 110 on which a metal film 112 is formed, a light source 120 that emits a light beam α towards the prism unit 110, a light receiving unit 130 that measures the light beam α reflected by the prism unit 110, and fluorescence detection means 140 for detecting light (fluorescence) based on an intensified electric field in the vicinity of the metal film 112.

The prism unit 110 is provided with a triangular prism (to be simply referred to as a "prism") 114, a metal film 112 deposited on a prescribed surface 114b opposing the vertical angle of the prism 114, an antibody solid layer film 113 deposited on the surface 112a of the metal film 112 (on the opposite side from the prism 114) and in which an antibody that captures a specific antigen in a specimen (sample solution) is immobilized on the surface thereof, and a flow path member 117 having a flow path 116 enabling the specimen to flow while contacting the surface of the antibody solid layer film 113.

In this prism unit 110, the prism 114 causes the light beam α emitted from the light source 120 to enter the prism 114 from one inclined surface (incident surface) 114a thereof, and the light beam α reflected by the metal film 112 provided on a prescribed surface 114b is emitted to the outside from the other inclined surface (emission surface) 114c. More specifically, the light beam α that has entered the prism 114 is totally reflected from the back side of the metal film 112 (side of the prism 114) at the surface 112a of the metal film 112, and is emitted outside the prism 114 from the emission surface 114c.

The light source 120 emits the light beam α towards the incident surface 114a of the prism 114. This light source 120 is composed so as to be able to change an angle of incidence θ of the light beam α relative to the metal film 112. The light receiving unit 130 receives the light beam α emitted outside the prism 114 from the emission surface 114c of the prism 114 as a result of being reflected by the metal film 12, and measures the intensity thereof. The fluorescence detection means 140 is arranged at a location opposing the metal film 112 with the flow path 116 interposed therebetween, and detects fluorescence of a fluorescent substance excited by an intensified electric field formed in the vicinity of the surface of the metal film 112.

Testing of a specimen is carried out in the manner described below in this fluorescence analysis device 100.

Figure 8:
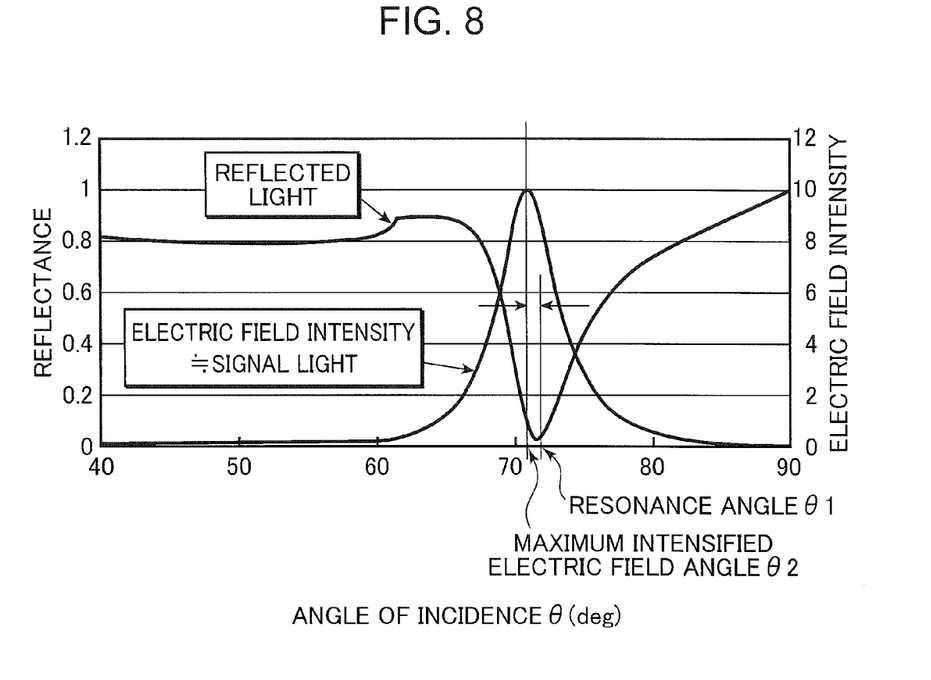
FIG. 8 is a drawing illustrating the relationship between reflectance of a light beam in a metal film of a prism unit and the intensity of plasmon scattered light generated in the vicinity of the surface of the metal film.

The fluorescence analysis device 100 determines the angle of incidence θ of the light beam α relative to the metal film 112 for forming an intensified electric field in the vicinity of the surface of the metal film 112 (and more precisely, the angle of incidence θ of the light beam α that enters the surface 112a of the metal film 112 from the back side 112b) prior to allowing a specimen to flow through the flow path 116. More specifically, the light beam α is emitted from the light source 120 while changing the angle of incidence θ of the light beam α relative to the metal film 112. At this time, the light beam α reflected by the metal film 112 is received by the light receiving unit 130, and the intensity thereof is measured. As a result, a resonance angle (SPR angle) θ1 is determined which is the angle of incidence relative to the metal film 112 at which surface plasmon resonance is generated in the metal film 112 (see FIG. 8). More specifically, the angle of incidence relative to the metal film 112 at which the intensity of reflected light is the lowest (namely, the angle of incidence at which reflectance is lowest) becomes resonance angle θ1. Here, as shown in FIG. 8, a shift occurs between the resonance angle θ1 at which surface plasmon resonance is generated in the metal film 112, and an angle of incidence θ2 of the light beam α relative to the metal film 112 at which the intensified electric field reaches a maximum (maximum intensified electric field angle). Namely, the resonance angle θ1 and the maximum intensified electric field angle θ2 do not coincide. Consequently, the fluorescence analysis device 100 determines an angle of incidence (measuring angle) θ3 when testing a specimen by adjusting (normally by ±05°) a prescribed angle from the determined resonance angle θ1.

The emitting direction of the light source 120 is adjusted so that the angle of incidence of the light beam α relative to the metal film 112 becomes the measuring angle θ3. As a result, the intensified electric field formed in the vicinity of the surface 112a of the metal film 112 (in the vicinity of the metal film 112 on the side of the flow path 116) roughly reaches a maximum. The specimen is then allowed to flow through the flow path 116 when in this state.

When the specimen flows through the flow path 116, a target substance (specific antigen) in the specimen is captured by antibody immobilized on the antibody solid layer film 112a by an antigen-antibody reaction. By then allowing a fluorescently labeled antibody to flow through the flow path 116, only the portion where antigen has been captured is labeled with the fluorescent substance. This labeled fluorescent substance emits light as a result of being excited by the intensified electric field formed in the vicinity of the surface of the metal film 112. As a result of this fluorescence being measured by the light receiving unit 130, the amount of antigen that has reacted in the fluorescence analysis device 100 can be measured with high sensitivity and high accuracy.

The amount of the angular shift between the resonance angle θ1 at which surface plasmon resonance is generated in the metal film 112 and the maximum intensified electric field angle θ2 at which the intensified electric field in the vicinity of the surface of the metal film 112 reaches a maximum is determined by various parameters. Thus, if some of the parameters differ, since this causes a change in the amount of shift between the resonance angle θ1 and the maximum intensified electric field angle θ2, even if the measuring angle θ3 is determined by accurately determining the resonance angle θ1 for each test, there are cases in which the intensified electric field formed in the vicinity of the surface of the metal film 112 does not reach a maximum. Namely, variations occur in the magnitude of the intensified electric field for each test in the fluorescence analysis device 100. Consequently, variations attributable to the fluorescence analysis device 100 may occur in measurement results even when testing the same specimen.

Patent Document 1: Japanese Patent Publication No. 4370383

SUMMARY OF THE INVENTION

An object of the present invention is to provide a surface plasmon resonance fluorescence analysis device and surface plasmon resonance fluorescence analysis method capable of accurately determining an angle of incidence of a light beam relative to a metal film of a prism unit such that a magnetic field for exciting a fluorescent substance contained in a specimen reaches maximum intensity.

The surface plasmon resonance fluorescence analysis device and surface plasmon resonance fluorescence analysis method according to the present invention radiate a light beam onto a prism so as to be reflected by a metal film formed on a prescribed surface of the prism, measure light resulting from the light beam being reflected by the metal film, and adjust the direction in which the light beam is emitted when measuring a specimen based on the intensity of the measured light. Consequently, according to the present invention, a surface plasmon resonance fluorescence analysis device and surface plasmon resonance fluorescence analysis method can be provided that are capable of accurately determining an angle of incidence of a light beam relative to a metal film of a prism unit such that an electric field for exciting a fluorescent substance contained in a specimen reaches maximum intensity.

The above-mentioned and other objects, characteristics and advantages of the present invention will be made clear from the following detailed description and appended drawings.

BEST MODE FOR CARRYING OUT THE INVENTION

The following provides a description of a first embodiment of the present invention with reference to the appended drawings.

Figure 1:
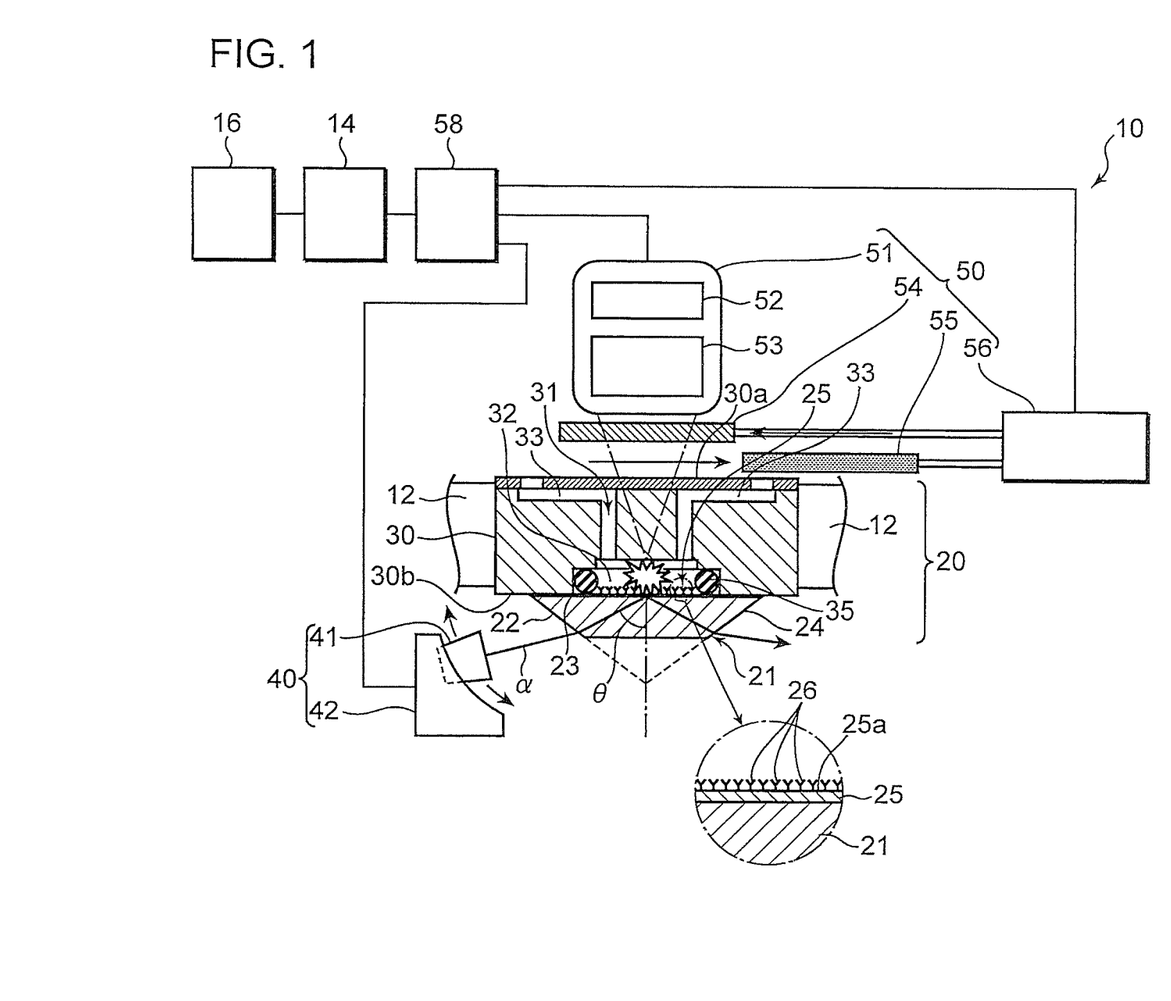
FIG. 1 is a schematic block diagram showing a surface plasmon resonance fluorescence analysis device according to a first embodiment.
Figure 2:
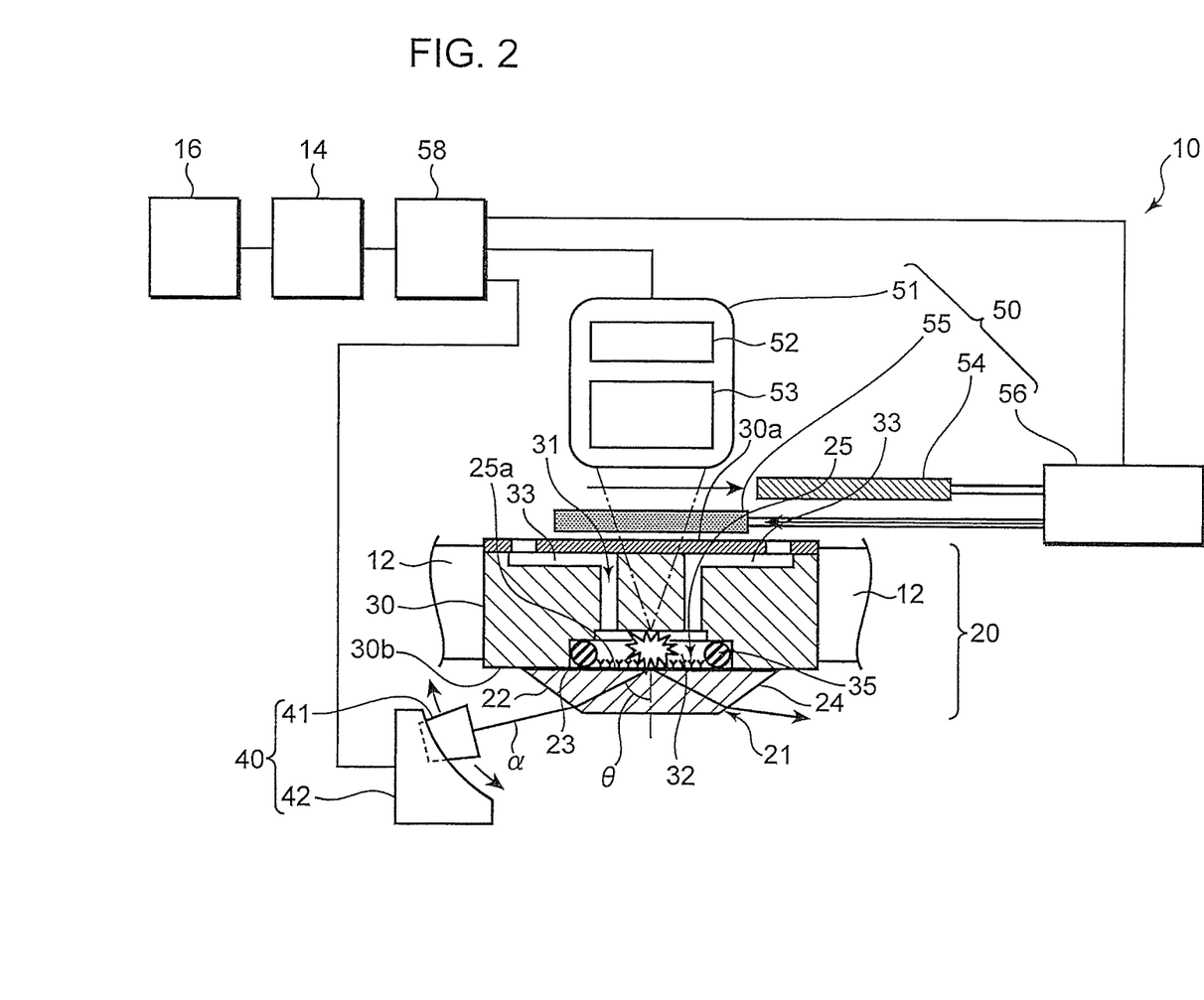
FIG. 2 is a schematic block diagram showing a state in which the positions of a first optical filter and a second optical filter have been switched in the surface plasmon resonance fluorescence analysis device.

As shown in FIGS. 1 and 2, the surface plasmon resonance fluorescence analysis device (to also be simply referred to as the "fluorescence analysis device") according to the present embodiment is provided with an analysis element tip (prism unit) 20, a light source 40 that emits a light beam towards the analysis element tip 20, a light measuring unit 50 that measures light generated in the analysis element tip 20, and a holder 12 that removably holds the analysis element tip 20. In addition, the fluorescence analysis device 10 is provided with a pretreatment unit (not shown) that carries out pretreatment of a specimen such as blood from a patient, an arithmetic processing unit 14 for analyzing light measured by the light measuring unit 50, and a display unit 16 for displaying various types of information such as arithmetic processing results of the arithmetic processing unit 14.

The analysis element tip 20 is provided with a prism 21, a metal film 25 formed on the surface of the prism 21, and a flow path member 30 that forms a flow path 31 that allows a specimen or sample solution such as a reagent or washing liquid (to be simply referred to as a "specimen") to flow over the metal film 25 while making contact therewith.

The prism 21 includes in the surfaces thereof an incident surface 22 where a light beam α from the light source 40 enters the prism 21, a deposition surface (prescribed surface) 23 where the metal film 25 is formed that reflects the light beam α that has entered the prism 21, and an emission surface 24 where the light beam α reflected by the metal film 25 is emitted outside the prism 21, and the prism 21 is formed from a transparent glass or resin. The prism 21 of the present embodiment is formed from a transparent glass or resin having a refractive index of about 1.40 to 1.75. Furthermore, the prism may have a shape of a triangle with the apex cut away when viewed from the side as in the present embodiment, or may have a shape of a triangle when viewed from the side (refer to the area indicated by the broken line in FIG. 1). Namely, the prism includes surfaces consisting of an incident surface, deposition surface and emission surface, and has a shape such that the light beam α that has entered the prism from the incident surface is totally reflected by the metal film on the deposition surface, after which the light beam α is emitted to the outside from the emission surface without being scattered or reflected inside.

The metal film 25 is a thin film made of a metal that is deposited (formed) on the deposition surface 23 of the prism 21. The metal film 25 of the present embodiment is formed from gold. This metal film 25 is a member for amplifying evanescent waves generated by total reflection of the light beam α. Namely, by providing the metal film 25 on the deposition surface 23 and generating surface plasmon resonance, the formed electric field can be intensified in comparison with evanescent waves being generated by total reflection of the light beam α by a surface not having the metal film 25 (deposition surface 23). Intensification of the electric field in the present embodiment (electric field intensity) is roughly 10 times greater than in the case of the metal film 25 not being present (see FIG. 3). The metal film 25 is formed to a film thickness of 30 nm to 70 nm by various types of deposition methods such as sputtering, vapor deposition or plating. Furthermore, the material of the metal film 25 is got limited to gold, but rather may be any of silver, copper or aluminum and the like (including alloys thereof) provided it is a metal that generates surface plasmons.

In addition, capturing bodies 26 for capturing a specific antigen are immobilized on a surface 25a of the metal film 25 (surface on the opposite side from the prism). These capturing bodies 26 are immobilized on the surface 25a of the metal film 25 by surface treatment.

The flow path member 30 is provided on the deposition surface 23 of the prism 21, and has the flow path 31 through which a specimen flows. This flow path member 30 is formed from a transparent resin. The flow path member 30 of the present embodiment is a plate-shaped member that extends in the horizontal direction. The flow path 31 is composed of a detecting portion 32 where an antigen-antibody reaction occurs, and guiding portions 33 that guide a specimen from outside the analysis element tip 20 to the detecting portion 32 or guide a specimen outside the analysis element tip 20 from the detecting portion 32. The detecting portion 32 is surrounded by a groove provided in a back side (lower side in FIG. 1) 30b of the flow path member 30 and the metal film 25 on the prism 21. Namely, in this detecting portion 32, the specimen flows while contacting the surface of the metal film 25 (surface on which the capturing bodies 26 are immobilized). One end of each guiding portion 33 opens to a surface 30a (upper surface in FIG. 1) of the flow path member 30, while the other end (end on the opposite side from the one end) is connected to the detecting portion 32. In this manner, a single flow path 31 is formed by sequentially connecting the guiding portion 33, detecting portion 32 and guiding portion 33.

This flow path member 30 is adhered (joined) to the prism 21 by an adhesive. In the present embodiment, a sealing member 35 composed of an elastic body is provided at a location that surrounds the detecting portion 32 from the horizontal direction while situated between the flow path member 30 and the prism 21. As a result, leakage of specimen from the site where the flow path member 30 and the prism 21 are joined is prevented. Furthermore, joining of the flow path member 30 and the prism 21 is not limited to the use of an adhesive, but rather the flow path member 30 and the prism 21 may be joined by laser welding, ultrasonic welding or press-fitting using a clamping member. In addition, the sealing member 35 surrounding the detecting portion 32 may be omitted if the flow path member 30 and the prism 21 are joined so as to be liquid-tight.

The light source 40 is a light source device that emits the light beam α towards the analysis element tip 20, and more precisely, towards the incident surface 22 of the prism 21. This light source 40 has a light emitting element 41 such as a semiconductor laser or LED, an angle changing unit 42 that changes the direction in which the light beam α is emitted by the light emitting element 41, and a polarizing plate (not shown) that polarizes the light beam α emitted from the light emitting element 41.

The angle changing unit 42 changes the direction in which the light beam α is emitted by the light emitting element 41 so as to change an angle of incidence θ of the light beam α relative to the metal film 25 (and more precisely, the surface 25a of the metal film 25) while in the state in which the light beam α emitted from the light emitting element 41 enters the prism 21 from the incident surface 22 and is totally reflected by the metal film 25 (and more precisely, the state in which the light beam α passes through the metal film 25 from the back side of the metal film 25 (side on the opposite side from the surface 25a) and is totally reflected by the surface 25a). More specifically, the angle changing unit 42 is composed so as to be able to change the emission direction of the light emitting element 41 so as to change the angle of incidence θ of the light beam α relative to the metal film 25 without changing the location where the light beam α is reflected in the metal film 25. The angle changing unit 42 of the present embodiment is connected to a control unit 58 of the light measuring means 50, and changes the direction in which the light beam α is emitted from the light emitting element 41 in accordance with an instruction signal from this control unit 58.

The polarizing plate polarizes the light beam α emitted from the light emitting element 41 so as to generate polarized light P relative to the metal film 25 provided on the deposition surface 23 of the prism 21. Furthermore, in the case of using a semiconductor laser for the light emitting element 41, it is not necessary to provide a polarizing plate if the semiconductor laser is arranged so that the plane of polarization of the semiconductor laser per se is aligned with the plane of polarization of polarized light P relative to the metal film 25.

The light measuring unit 50 is provided with a light receiving unit 51 that receives light generated on the side of the surface 25a of the metal film 25, a first optical filter 54, a second optical filter 55, a position switching device (position switching unit) 56 that respectively switches the position of the first optical 54 and the second optical filter 55, and the control unit 58 that controls each constituent of the light measuring unit 50, the angle changing unit 42 of the light source 40 and the like.

The light receiving unit 51 is composed of a light receiving element 52 that detects light, a lens and the like, and has optics 53 that guide light generated on the side of the surface 25a of the metal film 25 to the light receiving element 52. In the present embodiment, a photomultiplier tube is used for the light receiving element 52 in order to detect weak light (fluorescence generated by excitation of a fluorescent substance labeled to an antibody in a specimen).

The first optical filter 54 is an optical filter that emits incident light after attenuating that light. The first optical filter 54 of the present embodiment is a neutral density (ND) filter. As a result of this first optical filter 54 reducing plasmon scattered light generated in the metal film 25 of the analysis element tip 20, the plasmon scattered light can be measured by the light receiving element (photomultiplier in the present embodiment) 52 for detecting weak light.

The second optical filter 55 is an optical filter for blocking out light of a prescribed wavelength. The second optical filter 55 of the present embodiment is a longpass filter. Furthermore, the second optical filter 55 is not limited to a longpass filter, but may also be a bandpass filter and the like.

The second optical filter 55 prevents light of a wavelength (such as light (leak light) from the light source 40 or plasmon scattered light and the like) other than fluorescent light (light generated as a result of exciting a fluorescent substance labeled to an antigen in a specimen) from entering the light receiving unit 51. Namely, the second optical filter 55 serves to improve detection accuracy and detection sensitivity of weak fluorescence in the light receiving unit 51 by removing noise components from light entering the light receiving unit 51.

The position switching device 56 is a device for switching the positions of the first optical filter 54 and the second optical filter 55 between an intermediate position and a standby position. Furthermore, the intermediate position is a position between the metal film 25 and the light receiving unit 51. More specifically, the intermediate position is a position between the analysis element tip 20 and the light receiving unit 51 (position of the first optical filter 54 in FIG. 1). In addition, the standby position is a position farther away from the metal film 25 and the light receiving unit 51 than the intermediate position (position of the second optical filter 55 in FIG. 1). More specifically, the standby position is a position that allows light generated on the side of the surface 25a of the metal film 25 to enter the light receiving unit 51 directly.

More specifically, the position switching device 56 respectively switches the positions of the first optical filter 54 and the second optical filter 55 so that the second optical filter 55 is at the standby position when the first optical filter 54 is at the intermediate position (see FIG. 1), or so that the second optical filter 55 is at the intermediate position when the first optical filter 54 is at the standby position (see FIG. 2). This position switching device 56 is connected to the control unit 58, and switches the positions of the first optical filter 54 and the second optical filter 55 based on an instruction signal from this control unit 58.

Figure 3:
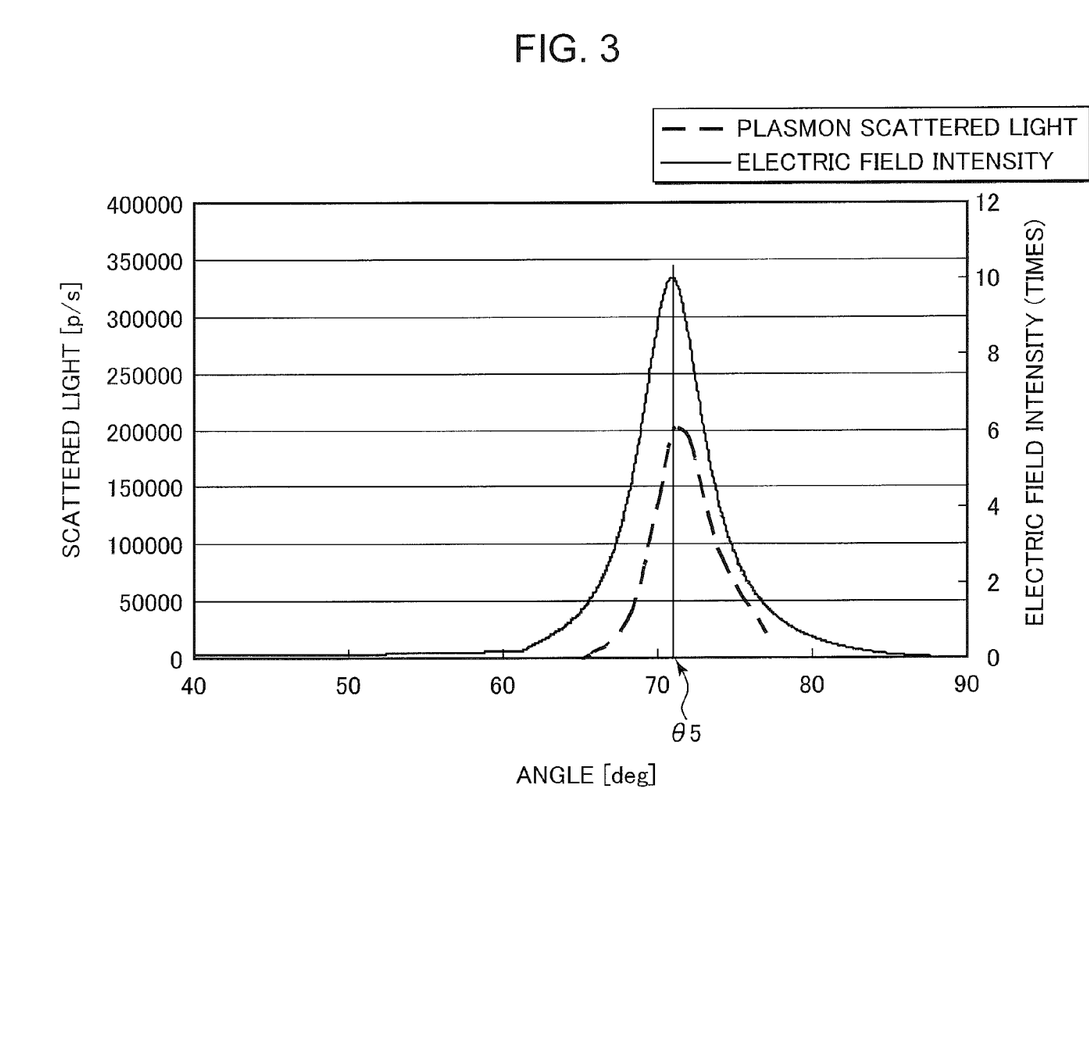
FIG. 3 is a drawing illustrating the relationship between the intensity of plasmon scattered light generated in the vicinity of the surface of a metal film formed on a prism and electric field intensity in the surface plasmon resonance fluorescence analysis device.

The control unit 58 controls each of the constituents of the light source 40 and the light measuring unit 50 and the like. More specifically, the control unit 58 adjusts the direction of the light beam α emitted by the light source 40 based on the intensity of light measured by the light receiving unit 51. The control unit 58 of the present embodiment adjusts the direction of the light beam α emitted by the light source 40 based on the intensity of plasmon scattered light generated on the side of the surface 25a of the metal film 25 of the analysis element tip 20. More specifically, the control unit 58 causes the light beam α to be emitted from the light source 40 so that the light beam α enters the metal film 25 while changing the angle of incidence θ from the back side (prism 21 side) of the metal film 25 to the metal film 25 by controlling the light emitting element 41 and the angle changing unit 42 of the light source 40 when the analysis element tip 20 is held in the holder 12. At this time, the light receiving unit 51 detects the intensity of plasmon scattered light generated on the side of the surface 25a of the metal film 25, and the control unit 58 adjusts the direction in which the light beam α is emitted from the light source 40 by controlling the angle changing unit 42 based on a change in this intensity. More specifically, when the light beam α enters the metal film 25 while changing the angle of incidence θ, the intensity of plasmon scattered light detected by the light receiving unit 51 changes as shown in FIG. 3. The control unit 58 determines the direction of the light beam α emitted from the light source 40 when the light beam α has entered the metal film 25 at an angle of incidence θ5 where this change in intensity reaches a peak (maximum value). The control unit 58 then outputs an instruction signal to the angle changing unit 42 so that the light source 40 can emit the light beam α in that direction by adjusting the orientation of the light source 41.

In addition, the control unit 58 issues instructions to the position switching device 56 to switch the positions of the first optical filter 54 and the second optical filter 55. More specifically, the control unit 58 outputs an instruction signal to the position switching device 56 so that the first optical filter 54 is at the intermediate position and the second optical filter 55 is at the standby position when adjusting the emission direction of the light beam α from the light source 40 using the aforementioned plasmon scattered light. On the other hand, the control unit 58 outputs an instruction signal to the position switching device 56 so that the first optical filter 54 is at the standby position and the second optical filter 55 is at the intermediate position when testing a specimen in the fluorescence analysis device 10.

The holder 12 is a site that holds the analysis element tip 20 when testing a specimen. More specifically, this holder 12 removably holds the analysis element 20 so that the analysis element tip 20 is in a prescribed orientation with respect to the light source 40. The prescribed orientation refers to an orientation in which the light beam α emitted from the light source 40 enters the prism 21 from the incident surface 22 and the light beam α that has entered the prism 21 is totally reflected by the metal film 25.

Figure 4:
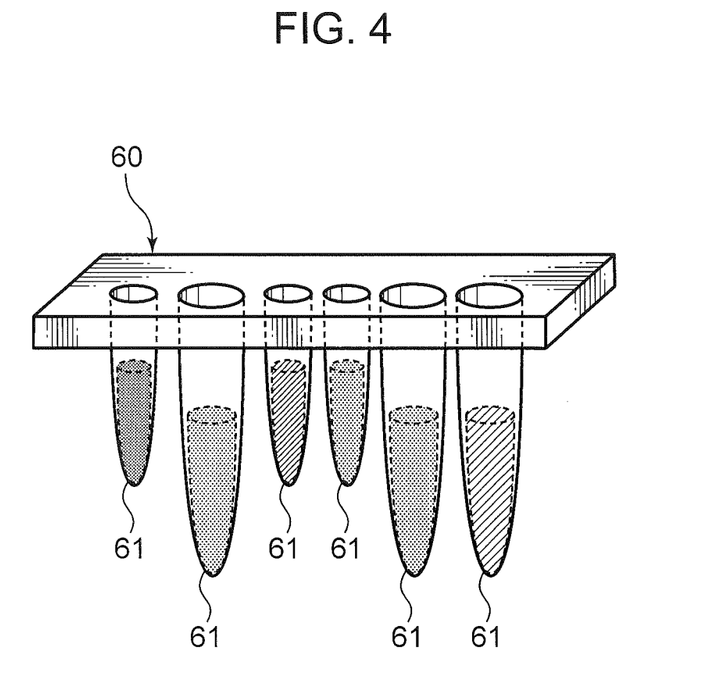
FIG. 4 is an enlarged perspective view explaining a reagent tip.

The pretreatment unit is a site that receives a reagent tip 60 (see FIG. 4), carries out pretreatment (such as blood cell separation, dilution or mixing and the like) on blood and the like serving as a testing target injected into the reagent tip 60, and injects the pretreated specimen into the analysis element tip 20. A plurality of housing units 61 are provided for the reagent tip 60, and reagent, diluent or washing liquid and the like are individually enclosed in each housing unit 61 in addition to blood and the like.

The arithmetic processing unit 14 is a site for arithmetically processing output signals sent from the light measuring unit 50 (light receiving unit 51) when testing a specimen, and carrying out analyses relating to fluorescence measured by the light measuring unit 50. More specifically, the arithmetic processing unit 14 carries out arithmetic processing on, for example, the number of counts of fluorescence per unit area as detected by the light measuring unit 50 or on the amount of increase in fluorescence with the passage of time. The results of arithmetic processing by the arithmetic processing unit 14 are output to the display unit 16 connected to this arithmetic processing unit 14.

The display unit 16 displays arithmetic processing results based on output signals from the arithmetic processing unit 14. The display unit 16 may be that which displays the results on a screen in the manner of a monitor and the like, or may be that which prints out results in the manner of a printer and the like. In addition, the display unit 16 may be a combination thereof.

Specimens are tested in the manner described below in the fluorescence analysis device 10 configured in this manner.

A specimen such as blood from a patient is collected, and the collected specimen is injected into the reagent tip 60. The reagent tip 60 injected with the specimen is then placed in the pretreatment unit of the fluorescence analysis device 10.

The pretreatment unit carries out pretreatment (such as blood cell separation, dilution or mixing and the like) on the reagent tip 60 placed therein.

Next, the fluorescence analysis device 10 determines a measuring angle which is the angle of incidence of the light beam α relative to the metal film 25 when testing the sample.

More specifically, the control unit 58 respectively switches the positions of the first optical filter 54 and the second optical filter 55 so that the first optical filter 54 is at the intermediate position and the second optical filter 55 is at the standby position by outputting an instruction signal to the position switching device 56 (see FIG. 1).

After the specimen having undergone pretreatment as described above in the fluorescence analysis device 10 is injected into the analysis element tip 20, the control unit 58 changes the angle of incidence θ of the light beam α entering the metal film 25 of the prism 21 with the angle changing unit 42 while causing the light source 40 to emit the light beam α. At this time, as a result of the light beam α entering the prism 21 and the light beam α passing through the metal film 25 from the back side of the metal film 25 and being totally reflected at the surface 25a thereof, evanescent waves exude to the side of the surface 25a of the metal film 25, thereby resulting in the generation of plasmon scattered light. The light measuring unit 50 (and more precisely, the light receiving element (photomultiplier tube) 52) measures the intensity of this plasmon scattered light. At this time, since the first optical filter 54 is arranged at the intermediate position, the plasmon scattered light generated on the side of the surface 25a of the metal film 25 reaches the light receiving element 52 in a reduced state as a result of passing through the first optical filter 54. Consequently, damage to the light receiving element 52 as a result of entry of intense light (and more precisely, light more intense than the fluorescence measured when testing a specimen) is prevented.

The control unit 58 determines the angle of incidence θ5 at which the intensity of plasmon scattered light reaches a maximum based on angle dependence data (data representing the relationship between the angle of incidence θ of the light beam α relative to the metal film 25 and optical intensity: see FIG. 3) for plasmon scattered light measured by the light measuring unit 50. Once the angle of incidence θ5 of the light beam α relative to the metal film 25 at which the intensity of plasmon scattered light reaches a maximum is determined, the control unit 58 is able to accurately derive the angle of incidence θ of the light beam α relative to the metal film 25 at which electric field intensity reaches a maximum. This is based on the fact that plasmon scattered light reaches a maximum when the magnitude of an electric field (electric field intensity) formed in the vicinity of the surface 25a of the metal film 25 that induces surface plasmon resonance reaches a maximum.

The control unit 58 then adjusts the direction of the light beam α emitted from the light source 40 so that the angle of incidence at which the light beam α enters the metal film 25 becomes the angle of incidence θ5 at which the intensity of plasmon scattered light reaches a maximum (namely, the angle of incidence θ5 at which electric field intensity reaches a maximum) by controlling the angle changing unit 42.

Next, the control unit 58 switches the positions of each of the optical filters 54 and 55. Namely, the position switching device 56 respectively switches the positions of the first optical filter 54 and the second optical filter 55 so that the first optical filter 54 is at the standby position and the second optical filter 55 is at the intermediate position according to instruction signal from the control unit 58 (see FIG. 2).

When the direction in which the light beam α is to be emitted when testing a specimen has been determined and the positions of the first optical filter 54 and the second optical filter 55 have been switched in this manner, the fluorescence analysis device 10 carries out an antigen-antibody reaction and the like in the detecting portion 32 of the flow path 31. At this time, the fluorescence analysis device 10 causes the light beam α to be emitted from the light source 40 in the adjusted direction. This light beam α causes the generation of surface plasmon resonance in the metal film 25, and an intensified electric field is generated in the detecting portion 32 of the flow path 31 by evanescent waves generated by this surface plasmon resonance.

In the detecting portion 32 of the flow path 31, a specific antigen in the specimen that flows through the flow path 31 is captured by the capturing bodies 26 immobilized on the surface 25a of the metal film 25. As a result of antibody labeled with a fluorescent substance flowing through the flow path 31, antigen captured by the capturing bodies 26 is labeled with the fluorescent substance. At this time, since an intensified electric field is formed in the vicinity of the surface 25a of the metal film 25 of the detecting portion 32, the fluorescent substance labeled to the antigen is excited by this electric field causing it to emit light.

This fluorescence is passed through the second optical filter 55, and noise components are consequently removed. Thereafter, it reaches the light receiving unit 51 where the fluorescence that has been removed of the noise components is detected by the light receiving element 52 of the light receiving unit 51. The light receiving unit 51 then outputs the result of this detection in the form of an output signal to the arithmetic processing unit 14 via the control unit 58. The arithmetic processing unit 14 receives this output signal and carries out a quantitative analysis on the antigen by arithmetically processing this output signal. Furthermore, when the light measuring unit 50 measures the fluorescence, the control unit 58 may continue to emit the light beam α from the light source 40 while allowing the specimen to flow through the flow path 31 in order to measure changes in the number of counts of fluorescence with the passage of time or measure changes in the number of counts of fluorescence before and after the specimen flows through the flow path 31. In addition, after the specimen has finished flowing through the flow path 31, the control unit 58 may wash the inside of the flow path 31 with a washing agent and subsequently cause light to be emitted by the light source 40 and enable the light measuring unit 50 to detect fluorescence from the fluorescent substance labeled to antigen captured by the capturing bodies 26.

The arithmetic processing unit 14 then sends the results of arithmetic processing to the display unit 16 and the display means 16 displays the results of arithmetic processing.

In this manner, after having determined the angle of incidence of the light beam α relative to the metal film 25 when testing a specimen based on plasmon scattered light in the form of the measuring angle θ5, the fluorescence analysis device 10 is able to accurately obtain the maximum electric field intensity angle θ5 at which the intensified electric field formed in the vicinity of the surface 25a of the metal film 25 reaches a maximum. Consequently, the fluorescence analysis device 10 is able to maximize the intensity of the intensified electric field in the vicinity of the surface 25a of the metal film 25 when testing a specimen. As a result, the fluorescence analysis device 10 is able to effectively cause a fluorescent substance contained in the specimen to emit light, and as a result thereof, the specimen can be detected with high sensitivity and high accuracy. Moreover, even if various parameters in the fluorescence analysis device 10 are changed, the fluorescence analysis device 10 is able to accurately obtain the angle of incidence θ5 of the light beam α relative to the metal film 25 at which electric field intensity in the vicinity of the surface 25a of the metal film 25 reaches a maximum, thereby making it possible to inhibit variations in the results of each test.

In addition, in the fluorescence analysis device 10, it is not necessary to measure the light beam α after having been reflected by the metal film 25 of the analysis element tip as in surface plasmon resonance fluorescence analysis devices of the prior art (namely, it is not necessary to determine plasmon resonance angle). Consequently, the fluorescence analysis device 10 is not required to be provided with optics for measuring the light beam α reflected by the metal film 25, thereby making it possible to reduce the size of the device and conserve costs.

Figure 5:
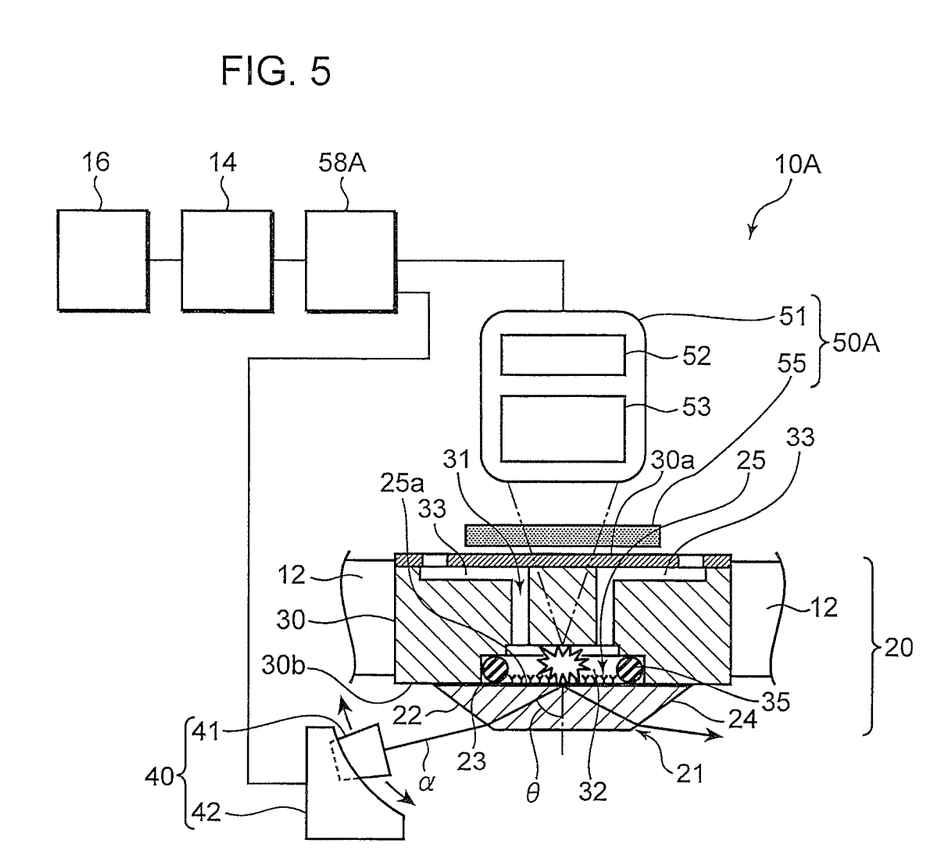
FIG. 5 is a schematic block diagram showing a surface plasmon resonance fluorescence analysis device according to a second embodiment.

Next, although the following provides a description of a second embodiment of the present invention with reference to FIG. 5, the same reference symbols are given those constituents of the second embodiment that are similar to those of the first embodiment, description thereof is omitted, and detailed description is only provided for those constituents that differ from the first embodiment.

The fluorescence analysis device 10A according to the present embodiment is provided with the analysis element tip (prism unit) 20, the light source 40, a light measuring unit 50A, the holder 12, a pretreatment unit (not shown), the arithmetic processing unit 14 and the display unit 16.

The light measuring unit 50A is provided with the light receiving unit 51, the optical filter 55 and a control unit 58A. The optical filter 55 is an optical filter for blocking out light of a prescribed wavelength, and is arranged at an intermediate position. The optical filter 55 of the present embodiment is a longpass filter.

The control unit 58A controls each of the constituents of the light source 40 and light measuring unit 50A and the like. When a specimen is injected into the analysis element tip 20 that is held in the holder 12, the control unit 58A of the present embodiment causes the light beam α to be emitted so that the light beam α enters the metal film 25 while changing the angle of incidence θ relative to the metal film 25 by controlling the light emitting element 41 of the light source 40 and the angle changing unit 42. At this time, the light receiving unit 51 detects fluorescence generated on the side of the surface 25a of the metal film 25, and the control unit 58A adjusts the direction in which the light beam α is emitted by the light source 40 by controlling the angle changing unit 42 based on a change in this intensity. Furthermore, fluorescence is generated as a result of antigen present in a specimen being captured by antibody on the metal film surface 25a as a result of the specimen flowing through the analysis element tip 20, and a fluorescent substance labeled to the captured antigen being excited by an intensified electric field formed by surface plasmon resonance generated in the metal film 25.

More specifically, when a specimen flows through the flow path 31 and the light beam α enters the metal film 25 while changing the angle of incidence θ relative to the metal film 25, the intensity of fluorescence detected in the light receiving unit 51 increases or decreases accompanying a change in the angle of incidence θ in the same manner as the change in intensity of plasmon scattered light shown in FIG. 3. The control unit 58A determines the direction at which the light beam α is emitted from the light source 40 so that the angle of incidence of the light beam α relative to the metal film 25 becomes the angle of incidence θ5 at which the change in intensity reaches a peak (maximum value). The control unit 58A then adjusts the orientation of the light emitting element 41 and outputs an instruction signal to the angle changing unit 42 so that the light source 40 is able to emit the light beam α in the determined direction.

Specimens are tested in the manner described below in the fluorescence analysis device 10A configured in this manner.

The reagent tip 60 injected with a specimen is placed in the pretreatment unit of the fluorescence analysis device 10A, and pretreatment (such as blood cell separation, dilution or mixing and the like) is carried out on the specimen.

The fluorescence analysis device 10A causes the pretreated specimen to be injected into the analysis element tip 20 and carries out an antigen-antibody reaction and the like in the detecting portion 32 of the flow path 31. At this time, the fluorescence analysis device 10 injects the specimen into the analysis element tip 20 and determines the measuring angle, namely the direction in which the light beam α is emitted from the light source 40 during specimen testing.

More specifically, the control unit 58A changes the angle of incidence θ of the light beam α that enters the metal film 25 provided on the deposition surface 23 of the prism 21 with the angle changing unit 42 while emitting the light beam α from the light source 40. At this time, since the light beam α is totally reflected by the metal film 25 (and more precisely, the surface 25a of the metal film 25), an electric field is formed by evanescent waves in the vicinity of the surface 25a of the metal film 25. On the other hand, the capturing bodies 26 immobilized on the metal film 25 capture antigen by an antigen-antibody reaction and the like in the detecting portion 32 of the flow path 31. When a fluorescent substance is labeled to the captured antigen, the fluorescent substance is excited by the electric field formed in the vicinity of the surface 25a of the metal film 25 resulting in emission of light.

The light measuring unit 50 (and more precisely, the light receiving element 52) measures the intensity of this fluorescence. At this time, since fluorescence from which noise components have been removed by the optical filter 55 enters the light receiving unit 51 of the light measuring unit 50, weak fluorescence is measured with high sensitivity and high accuracy.

The control unit 58A determines the angle of incidence θ5 of the light beam α relative to the metal film 25 at which the intensity of fluorescence reaches a maximum based on angle dependence data (data representing the relationship between the angle of incidence θ of the light beam α relative to the metal film 25 and optical intensity) for fluorescence measured by the light measuring unit 50. Once the angle of incidence θ5 of the light beam α relative to the metal film 25 at which the intensity of fluorescence reaches a maximum is determined, the control unit 58A is able to accurately derive the angle of incidence θ of the light beam α relative to the metal film 25 at which electric field intensity reaches a maximum. This is because the intensity of fluorescence emitted by the excited fluorescent substance changes based on the intensity of the electric field.

The control unit 58A then adjusts the direction of the light beam α emitted from the light source 40 so that the angle of incidence at which the light beam α enters the metal film 25 becomes the angle of incidence at which the intensity of fluorescence reaches a maximum, namely the angle of incidence θ5 at which electric field intensity reaches a maximum, by controlling the angle changing unit 42.

The specimen is continued to be injected into the analysis element chip 20, and fluorescence generated in the detecting portion 32 of the analysis element tip 20 is continued to be measured, even after the direction of emission of the light beam α from the light source 40 has been adjusted.

More specifically, the light receiving unit 51 detects fluorescence generated in the detecting portion 32, and outputs the result of this detection in the form of an output signal to the arithmetic processing unit 14 via the control unit 58A. The arithmetic processing unit 14 receives this output signal and carries out quantitative processing on the antigen by arithmetically processing this output signal. The arithmetic processing unit 14 then sends the result of arithmetic processing to the display unit 16, and the display unit 16 displays this arithmetic processing result.

In this manner, after having determined the measuring angle θ5 based on fluorescence, the fluorescence analysis device 10A is also able to accurately obtain the maximum electric field intensity angle θ5 at which the intensified electric field formed in the vicinity of the surface 25a of the metal film 25 reaches a maximum. Consequently, the fluorescence analysis device 10A is able to maximize the intensity of the intensified electric field in the vicinity of the surface 25a of the metal film 25 when testing a specimen, and as a result of effectively causing a fluorescent substance contained in the specimen to emit light as a result thereof, the specimen can be detected with high sensitivity and high accuracy. Moreover, even if various parameters in the fluorescence analysis device 10A are changed, the fluorescence analysis device 10A is able to accurately obtain the angle of incidence θ5 of the light beam α relative to the metal film 25 at which electric field intensity in the vicinity of the surface 25a of the metal film 25 reaches a maximum. As a result, the fluorescence analysis device 10A is able to inhibit variations in the results of each test.

In addition, unlike the fluorescence analysis device 10 of the first embodiment, since it is not necessary to measure plasmon scattered light in order to determine the measuring angle θ5 in the fluorescence analysis device 10A, the first optical filter 54 and the position switching device 56 for the first optical filter 54 and the second optical filter 55 (see FIG. 1) are also not required to be provided. Consequently, the fluorescence analysis device 10A makes it possible to reduce the size of the device and conserve costs.

Furthermore, the surface plasmon resonance fluorescence analysis device and surface plasmon resonance fluorescence analysis method of the present invention are not limited to the first and second embodiments, but rather various modifications can naturally be added within a range that does not deviate from the gist of the present invention.

For example, although the analysis element tip 20 is included in the configurations of the fluorescence analysis devices 10 and 10A in the aforementioned first and second embodiments, the fluorescence analysis device may also not be included in the configurations of these fluorescence analysis devices. Namely, a fluorescence analysis device may be configured so as to carry out testing by using an analysis element tip used in another analysis device.

Although the fluorescence analysis device 10 of the first embodiment is provided with the first optical filter 54 and the position switching device 56 for switching the position of this optical filter in order to measure plasmon scattered light and fluorescence with the common light receiving element (photomultiplier tube) 52, it is not limited thereto. Namely, a fluorescence analysis device may be provided with a light receiving element (such as a CCD) for receiving intense light (plasmon scattering light) and a light receiving element (such as a photomultiplier tube) for receiving weak light (fluorescent light) instead of using the first optical filter 54, and may be configured so as to switch the positions of these light receiving elements according to the light to be measured.

SUMMARY OF THE EMBODIMENTS

The following provides a summary of the embodiments.

The surface plasmon resonance fluorescence analysis device according to the embodiment is a surface plasmon resonance fluorescence analysis device that measures fluorescence emitted as a result of a fluorescent substance contained in a specimen being excited by an electric field based on surface plasmon resonance, and is provided with a prism unit having a prism in which a metal film is formed on a prescribed surface thereof, a light source that emits a light beam into the prism from a surface different from the prescribed surface so as to be reflected by the metal film, a light measuring unit capable of measuring an intensity of light generated in the metal film on an opposite side from the prism as a result of the light beam being reflected by the metal film, and a control unit that adjusts a direction in which the light beam is emitted from the light source based on the intensity of light measured by the light measuring unit.

According to this configuration, an angle of incidence of a light beam relative to a metal film (namely, the direction in which the light beam is emitted by the light source) is accurately obtained at which the intensity of an electric field formed in the vicinity of the surface of the metal film (on the side opposite from the prism) by surface plasmon resonance reaches a maximum. Consequently, when testing a specimen, the electric field intensity in the vicinity of the surface of the metal film can be maximized, and as a result of being able to effectively cause a fluorescent substance contained in the specimen to emit light as a result thereof, the specimen can be tested with high sensitivity and high accuracy. Moreover, even if various parameters in the fluorescence analysis device are changed, the fluorescence analysis device is able to accurately obtain the angle of incidence of the light beam relative to the metal film at which electric field intensity in the vicinity of the surface of the metal film reaches a maximum, thereby making it possible to inhibit variations in the results of each test.

Moreover, in this fluorescence analysis device, it is not necessary to measure the light beam after having been reflected by a prescribed surface of the prism unit in the manner of surface plasmon resonance fluorescence analysis devices of the prior art. Consequently, the fluorescence analysis device is not required to be provided with optics for measuring the reflected light beam, thereby making it possible to reduce the size of the fluorescence analysis device and conserve costs.

In the surface plasmon resonance fluorescence analysis device, the light measuring unit may measure an intensity of plasmon scattered light generated in the metal film, or capturing bodies capable of capturing a specific antigen contained in the specimen may be immobilized on the metal film on the opposite side from the prism, and the light measuring unit may measure an intensity of fluorescence of the fluorescent substance based on the specific antigen captured by the aforementioned capturing bodies.

Regardless of whether using plasmon scattered light generated in a metal film prior to testing a specimen or using light generated in the vicinity of the surface of the metal film during testing of a specimen, an angle of incidence of a light beam relative to the metal film is accurately obtained at which the intensity of an electric field formed in the vicinity of the surface of the metal film by surface plasmon resonance reaches a maximum. Furthermore, the light generated in the vicinity of the surface of the metal film is fluorescent light generated due to excitation of a fluorescent substance labeled to a specific antigen in the specimen that has been captured by capturing bodies on the surface of the metal film.

In the case of using plasmon scattered light to determine the angle of incidence of a light beam relative to a metal film when testing a sample (namely, the measuring angle), the light measuring unit preferably has a light receiving unit that receives light generated in the metal film, a first optical filter that emits incident light after attenuating that light, and a position switching unit that switches a position of the first optical filter between an intermediate position that is located between the metal film and the light receiving unit, and a standby position that is farther away from the metal film and the light receiving unit than the intermediate position.

According to this configuration, plasmon scattered light for determining the angle of incidence of a light beam relative to a metal film at which magnetic field intensity in the vicinity of the surface of the metal film reaches a maximum, and fluorescence of a fluorescent substance contained in a specimen, can be measured by a common light receiving unit. More specifically, plasmon scattered light refers to light having an extremely large amount of light as compared with the amount of light when a fluorescent substance labeled to an antigen is made to emit light. Consequently, by reducing this plasmon scattered light by passing through the first optical filter when measuring this plasmon scattered light, a light receiving unit for measuring fluorescence is able to measure plasmon scattered light.

In addition, the light measuring unit preferably has a second optical filter that blocks out light of a prescribed wavelength, and the position switching unit is preferably able to respectively switch the positions of the first optical filter and the second optical filter so that the second optical filter is at the standby position when the first optical filter is at the intermediate position, or so that the second optical filter is at the intermediate position when the first optical filter is at the standby position.

According to this configuration, plasmon scattered light and fluorescence of a fluorescent substance contained in a specimen can be measured with a common light receiving unit, and weak light in the form of fluorescent light is measured with high sensitivity and high accuracy. Namely, plasmon scattered light reaches the light receiving unit after having been reduced as a result of moving the first optical filter to the intermediate position during measurement of plasmon scattered light, while light of a wavelength other than that of fluorescent light (noise components) is blocked from entering the light receiving unit as a result of moving the second optical filter to the intermediate position, thereby further improving sensitivity and accuracy when measuring fluorescence.

On the other hand, in the case of using light that has been generated by exciting a fluorescent substance contained in a specimen (fluorescence) to determine the measuring angle, the light measuring unit preferably has a light receiving unit that receives light generated in the metal film and an optical filter that blocks out light of a prescribed wavelength, and the optical filter is preferably arranged at an intermediate position between the metal film and the light receiving unit.

According to this configuration, light of a wavelength other than that of fluorescent light (noise components) is blocked from entering the light receiving unit, and weak light in the form of fluorescence is measured with higher sensitivity and higher accuracy.

In addition, the surface plasmon resonance fluorescence analysis device according to the embodiment is a surface plasmon resonance fluorescence analysis device that measures fluorescence emitted as a result of a fluorescent substance contained in a specimen being excited by an electric field based on surface plasmon resonance, and is provided with a holder that removably holds a prism unit having a prism in which a metal film is formed on a prescribed surface thereof, a light source capable of emitting a light beam towards the prism when the prism is held in the holder, a light measuring unit capable of measuring an intensity of light generated in the metal film on an opposite side from the prism as a result of the light beam being reflected by the metal film of the prism unit when the prism unit is held in the holder, and a control unit that adjusts a direction in which the light beam is emitted from the light source based on the intensity of light measured by the light measuring unit. The holder holds the prism unit in such a manner that the light beam emitted from the light source enters the prism and the light beam that has entered is reflected by the metal film.

According to this configuration, as a result of holding the prism unit in the holder, the angle of incidence of the light beam relative to the metal film (namely, the direction in which the light beam is emitted by the light source), at which the intensity of an electric field formed in the vicinity of the surface of the metal film (side on the opposite side from the prism) by surface plasmon resonance reaches a maximum, is accurately obtained.

In the surface plasmon resonance fluorescence analysis method, an intensity of plasmon scattered light generated in the metal film may be measured in the light measuring step, or the metal film may have capturing bodies that are capable of capturing a specific antigen contained in the specimen and are immobilized on the side opposite from the prism, and an intensity of fluorescence of the fluorescent substance based on the specific antigen captured by the capturing bodies may be measured in the light measuring step.

Regardless of whether using plasmon scattered light generated in a metal film prior to testing a specimen or using light generated in the vicinity of the surface of the metal film during testing of a specimen, an angle of incidence of a light beam relative to the metal film is accurately obtained at which the intensity of an electric field formed in the vicinity of the surface of the metal film by surface plasmon resonance reaches a maximum.

INDUSTRIAL APPLICABILITY

As has been described above, the surface plasmon resonance fluorescence analysis device and surface plasmon resonance fluorescence analysis method according to the present invention is useful for causing a fluorescent substance contained in a specimen to emit light by utilizing a magnetic field of evanescent waves generated by surface plasmon resonance, and measuring the specimen by detecting this fluorescence, and is suitable for accurately determining an angle of incidence of a light beam relative to a metal film of a prism unit such that the electric field of evanescent waves reaches a maximum.

The invention claimed is:
1. A surface plasmon resonance fluorescence measurement device that measures fluorescence emitted as a result of a fluorescent substance labeled to a specific antigen con- tained in a specimen being excited by an electric field based on surface plasmon resonance, comprising:
- a prism unit having a prism in which a metal film having a thickness is formed on a prescribed surface thereof;
- a light source having a light emitting element that emits a light beam onto the prism from a surface different from the prescribed surface so as to cause the light beam to be incident on a first surface of the metal film facing the prescribed surface and be reflected by the metal film, and an angle changing unit configured to change a direction in which the light beam is emitted by the light emitting element so as to change an angle of incidence of the light beam relative to the metal film;
- a light measuring unit configured to measure an intensity of light generated on a second surface of the metal film that is opposite to the first surface of the metal film and facing the light measuring unit, as a result of the light beam being reflected by the metal film, the light measuring unit comprising:
  - a light receiving unit configured to receive light;
  - a first optical filter that is a neutral density filter configured to attenuate light;
  - a second optical filter configured to block out noise components except fluorescence emitted by excitation of the fluorescent substance; and
  - a position switching unit configured to switch positions of the first optical filter and the second optical filter between an intermediate position that is in a region interposed between the metal film and the light receiving unit, and a standby position that is outside the region,
  - wherein the light receiving unit receives plasmon scattered light through the neutral density filter located at the intermediate position and receives the fluorescence of the fluorescent substance labeled to the specific antigen when the second optical filter is at the intermediate position; and
  - wherein the position switching unit is configured to respectively switch the positions of the first optical filter and the second optical filter so that the second optical filter is at the standby position when the first optical filter is at the intermediate position, or so that the second optical filter is at the intermediate position when the first optical filter is at the standby position; and
- a control unit configured to control the position switching unit and to control the angle changing unit;
- wherein the control unit is configured to control the position switching unit so that the first optical filter is at the intermediate position and the second optical filter is at the standby position, is configured to control the angle changing unit so that the light beam emitted from the light emitting element enters the metal film while changing an angle of incidence to the metal film, is configured to cause the plasmon scattered light generated on the first surface surface of the metal film to pass through the first optical filter while emitting the light beam from the light emitting element, thereby measuring the intensity of plasmon scattered light having passed through the first optical filter, and is configured to determine the angle of incidence of the light beam emitted from the light emitting element so that the intensity of plasmon scattered light measured by the light measuring unit reaches a maximum value; and
- the control unit is configured to control the position switching unit so that the first optical filter is at the standby position and the second optical filter is at the intermediate position, is configured to control the angle changing unit to cause the light beam from the light emitting element to enter the metal film at the angle of incidence where the intensity of the plasmon scattered light reaches the maximum value, is configured to cause the fluorescence emitted by the fluorescent substance labeled to the specific antigen captured on the first surface of the metal film in the electric field based on the surface plasmon resonance generated on the first surface of the metal film to pass through the second optical filter, thereby measuring the intensity of the fluorescence having passed through the second optical filter.

2. The surface plasmon resonance fluorescence analysis device according to claim 1, wherein capturing bodies capable of capturing the specific antigen contained in the specimen are immobilized on the first surface of the metal film, and
the light measuring unit measures the intensity of fluorescence of the fluorescent substance based on the specific antigen captured by the capturing bodies.

3. The surface plasmon resonance fluorescence analysis device according to claim 2, wherein the second optical filter blocks out light of a prescribed wavelength.

4. A surface plasmon resonance fluorescence measurement device that measures fluorescence emitted as a result of a fluorescent substance labeled to a specific antigen contained in a specimen being excited by an electric field based on surface plasmon resonance, comprising:
- a holder that removably holds a prism unit having a prism in which a metal film having a thickness is formed on a prescribed surface thereof;
- a light source having a light emitting element configured to emit a light beam towards the prism when the prism is held in the holder so that the light beam is incident on a first surface of the metal film facing the prescribed surface, and an angle changing unit configured to change a direction in which the light beam is emitted by the light emitting element so as to change an angle of incidence of the light beam relative to the metal film;
- a light measuring unit configured to measure an intensity of light generated on a second surface of the metal film that is opposite the first surface of the metal film and facing the light measuring unit, as a result of the light beam being reflected by the metal film of the prism unit when the prism unit is held in the holder, the light measuring unit comprising:
  - a light receiving unit that receives light;
  - a first optical filter that is a neutral density filter configured to attenuate light;
  - a second optical filter configured to block out noise components except the fluorescence emitted by excitation of the fluorescent substance; and
  - a position switching unit configured to switch positions of the first optical filter and the second optical filter between an intermediate position that is in a region interposed between the metal film and the light receiving unit, and a standby position that is outside the region;
  - wherein the light receiving unit is configured to receive a plasmon scattered light through the neutral density filter located at the intermediate position and receive fluorescence of the fluorescent substance labeled to the specific antigen when the second optical filter is at the intermediate position; and
  - the position switching unit is configured to respectively switch the positions of the first optical filter and the second optical filter so that the second optical filter is at the standby position when the first optical filter is at the intermediate position, or so that the second optical filter is at the intermediate position when the first optical filter is at the standby position; and a control unit configured to control the position switching unit and to control the angle changing unit;

wherein the control unit is configured to control the position switching unit so that the first optical filter is at the intermediate position and the second optical filter is at the standby position, is configured to control the angle changing unit so that the light beam emitted from the light emitting element enters the metal film while changing an angle of incidence to the metal film, is configured to cause the plasmon scattered light generated on the first surface of the metal film to pass through the first optical filter while emitting the light beam from the light emitting element, thereby measuring the intensity of plasmon scattered light having passed through the first optical filter and is configured to determine the angle of incidence of the light beam emitted from the light emitting element so that the intensity of plasmon scattered light measured by the light measuring unit reaches a maximum value, and the control unit is configured to control the position switching unit so that the first optical filter is at the standby position and the second optical filter is at the intermediate position, is configured to control the angle changing unit to cause the light beam from the light emitting element to enter the metal film at the angle of incidence where the intensity of the plasmon scattered light reaches the maximum value, is configured to cause the fluorescence emitted by the fluorescence substance labeled to the specific antigen captured on the first surface of the metal film in the electric field based on the surface plasmon resonance generated on the first surface of the metal film to pass through the second optical filter, and is configured to measure the intensity of the fluorescence having passed through the second optical filter, wherein the holder holds the prism unit in such a manner that the light beam emitted from the light emitting element enters the prism and the light beam that has entered is reflected by the metal film.

5. A surface plasmon resonance fluorescence measurement method for measuring fluorescence emitted as a result of a fluorescent substance labeled to a specific antigen contained in a specimen being excited by an electric field based on surface plasmon resonance, comprising:

allowing a light beam to enter a prism in which a metal film having a thickness is formed on a prescribed surface thereof, from a surface different from the prescribed surface so that the light beam is incident on a first surface of the metal film facing the prescribed surface of the prism and reflected by the metal film, and emitting the light beam while changing an angle of incidence relative to the metal film in a state in which the light beam is reflected by the metal film;

measuring an intensity of plasmon scattered light through a first optical filter that is a neutral density filter by using a light receiving unit, the plasmon scattered light being generated on a second surface of the metal film that is opposite to the first surface of the metal film and facing the light receiving unit, as a result of the light beam being reflected by the metal film;

determining an angle of incidence at which the light beam enters the metal film at an angle of incidence where the intensity of plasmon scattered light measured reaches a maximum value;

emitting the light beam so that the light beam enters the metal film at the angle of incidence to thereby generate the surface plasmon resonance on the first surface of the metal film and cause the electric field based on the surface plasmon resonance; and switching positions of the first optical filter and a second optical filter between an intermediate position that is located in a region interposed between the metal film and the light receiving unit, and a standby position that is outside the region so that the first optical filter is at the standby position and the second optical filter is at the intermediate position, the second optical filter blocking out noise components except the fluorescence emitted by the fluorescent substance by excitation of the fluorescent substance labeling the fluorescent substance to the specific antigen captured on the first surface of the metal film by causing the specimen to flow in such a manner so as to come into contact with the first surface of the metal film receiving the fluorescence generated on the first surface of the metal film by the light receiving unit via the second optical filter, the fluorescence being generated in the metal film by the excitation of the labeled fluorescent substance in the electric field based on the surface plasma resonance, thereby measuring the intensity of the fluorescence by the light measuring unit.

6. The surface plasmon resonance fluorescence analysis method according to claim 5, wherein the metal film has capturing bodies that are capable of capturing the specific antigen contained in the specimen and are immobilized on the first surface of the metal film, and an intensity of fluorescence of the fluorescent substance based on the specific antigen captured by the capturing bodies is measured.

7. The surface plasmon resonance fluorescence analysis device according to claim 1, wherein capturing bodies capable of capturing the specific antigen contained in the specimen are immobilized on the first surface of the metal film, and the light measuring unit measures the intensity of fluorescence of the fluorescent substance based on the specific antigen captured by the capturing bodies.

8. The surface plasmon resonance fluorescence analysis device according to claim 7, wherein the second optical filter blocks out light of a prescribed wavelength.

* * * * *